(12) United States Patent
Piers et al.

(10) Patent No.: US 7,078,546 B2
(45) Date of Patent: Jul. 18, 2006

(54) 1,2-BIS(9-BORA-1,2,3,4,5,6,7,8-OCTAFLUOROFLUORENYL)-3,4,5,6-TETRAFLUROBENZENE AND RELATED COMPOUNDS AND METHODS

(75) Inventors: Warren Edward Piers, Calgary (CA); Preston A. Chase, Amsterdam (NL); Lee Douglas Henderson, Calgary (CA)

(73) Assignee: University Technologies International Inc., Calgary (CA)

( * ) Notice: Subject to any disclaimer, the term of this patent is extended or adjusted under 35 U.S.C. 154(b) by 68 days.

(21) Appl. No.: 10/817,753

(22) Filed: Apr. 2, 2004

(65) Prior Publication Data

US 2005/0222463 A1    Oct. 6, 2005

(51) Int. Cl.
    *C07F 7/26*    (2006.01)
(52) U.S. Cl. .................................. 556/7; 568/1; 568/3
(58) Field of Classification Search .................... 556/7; 568/1

See application file for complete search history.

(56) References Cited

U.S. PATENT DOCUMENTS 5,496,960 A * 3/1996 Piers et al. .................... 556/8

6,268,445 B1    7/2001 McAdon et al.

OTHER PUBLICATIONS

Chase et al., New Fluorinated 9-Borafluorene Lewis Acids, J. Am. Chem. Soc., 122 (51), 12911-12912, 2000.*
Lewis, S.P., et al., "Isobutene Polymerization Using a Chelating Diborane Co-Initiator," *J. Am. Chem. Soc. 125*(48):14686-14687, 2003.
Piers, W.E., et al., "Perfluoroaryl Boranes and Diboranes," *Proceedings of the 84th CSC Conference and Exhibition*, Multifunctional Lewis Acids Symposium, Montreal, Canada, May 26-30, 2001, 8 slides.
Williams., C., et al., New Bifunctional Perfluoroaryl Boranes. Synthesis and Reactivity of the *ortho*-Phenylene-Bridged Diboranes 1,2-[B($C_6F_5$)$_2$]$_2C_6X_4$ (X=H, F)', *J. Am. Chem. Soc. 121*(13):3244-3245, 1999.

* cited by examiner

*Primary Examiner*—Johann Richter
*Assistant Examiner*—Chukwuma Nwaonicha
(74) *Attorney, Agent, or Firm*—Christensen O'Connor Johnson Kindness PLLC

(57) ABSTRACT

The compound 1,2-bis(9-bora-1,2,3,4,5,6,7,8-octafluorofluorenyl)-3,4,5,6-tetrafluorobenzene, analogs of the compound, and methods for making the compound and its analogs.

13 Claims, 15 Drawing Sheets

$Ar^F = C_6F_5$ or $Ar^F_2 = C_{12}F_8$

I $Ar^F = C_6F_5$ or $Ar^F_2 = C_{12}F_8$ $Ar^F = C_6F_5$ or $Ar^F{}_2 = C_{12}F_8$ $Ar^F = C_6F_5$ or $Ar^F_2 = C_{12}F_8$

X = CH$_2$, NR, or O

Ar$^F$ = C$_6$F$_5$ or Ar$^F_2$ = C$_{12}$F$_8$

X = CH$_2$, NR, or O

Ar$^F$ = C$_6$F$_5$ or Ar$^F_2$ = C$_{12}$F$_8$ $Ar^F = C_6F_5$ or $Ar^F_2 = C_{12}F_8$ $Ar^F = C_6F_5$ or $Ar^F_2 = C_{12}F_8$ $Ar^F = C_6F_5$ or $Ar^F_2 = C_{12}F_8$

1,2-BIS(9-BORA-1,2,3,4,5,6,7,8-OCTAFLUOROFLUORENYL)-3,4,5,6-TETRAFLUROBENZENE AND RELATED COMPOUNDS AND METHODS

FIELD OF THE INVENTION

The present invention provides the compound 1,2-bis(9-bora-1,2,3,4,5,6,7,8-octafluorofluorenyl)-3,4,5,6-tetrafluorobenzene, analogs of the compound, and methods for making the compound and its analogs.

BACKGROUND OF THE INVENTION

Conventional methods of butyl rubber manufacture employ temperatures of −100° C. to −90° C., methyl chloride as a diluent, and a Lewis acid co-initiator such as aluminum chloride. Under these conditions, production of high molecular weight (typically greater than 200,000) butyl rubber, which is a co-polymer of isobutylene (i.e., isobutene) and 0.5–2.5 weight percent isoprene, occurs at acceptable rates and where water in combination with the Lewis acid is effective for protic initiation of polymerization. Methyl chloride is useful as it is both a polar solvent that enhances propagation rates and a poor solvent for butyl rubber so that the process is a suspension polymerization at these low temperatures. About 500 million pounds of butyl rubber was produced in the United States in 1991.

Legislation passed in the United States allows the use of methyl chloride in existing plants. However, expansion and/or construction of new plants will require the use of alternative solvents that are not chlorinated. Hence, there is a need to develop initiators that will be effective in the absence of a halogenated solvent in producing high molecular weight butyl rubber at commercially acceptable rates. Ideally, the process is a suspension polymerization so as to facilitate heat and mass transfer. Solution polymerization in liquid or diluted monomer and a supported catalyst are also possibilities.

A variety of Lewis acidic main group and transition metal initiators or co-initiators of isobutylene polymerization have been reported to provide poly(isobutene) (PIB) or co-polymers of isobutylene and isoprene in the absence of chlorinated solvents or with a minimum amount of chlorinated solvents being present. None of these compositions actually provide butyl rubber of sufficiently high molecular weight at acceptable rates in the absence of chlorinated solvents. Hence, there is a continuing need to develop more effective initiator compositions.

Chelating diboranes have been investigated as co-catalysts in combination with metallocene dialkyls in ethylene polymerization. Generically, these compounds can be formulated as $R'_2B$—$R$—$BR'_2$ where R is a covalent linking atom or group, R' is an organic substituent and R is of a length that allows the two boron (B) atoms to cooperate in the binding of suitable anions or donors. More specifically, R and R' are both perfluorinated alkyl groups, most preferably perfluoroaryl substituents so that the boron atoms are highly Lewis acidic, but hydrolytically stable and soluble in non-polar solvents. In addition, triphenylmethyl diborates ($[Ph_3C][R(BR'_3)_2(\mu-X)]$ with X=F, $N_3$, OMe, $OC_6F_5$, and R and R' as above) in which the diborate counter-anion has a group X bridging the two boron atoms were also investigated and some of these compositions were more effective as co-catalysts in ethylene polymerization than mononuclear versions such as $[Ph_3C][B(C_6F_5)_4]$, which is in commercial use.

SUMMARY OF THE INVENTION

In one aspect, the present invention provides 1,2-bis(9-bora-1,2,3,4,5,6,7,8-octafluorofluorenyl)-3,4,5,6-tetrafluorobenzene($1,2-[B(C_{12}F_8)]_2C_6F_4$). Analogs of 1,2-bis(9-bora-1,2,3,4,5,6,7,8-octafluorofluorenyl)-3,4,5,6-tetrafluorobenzene are also provided.

In another aspect of the present invention, a method for making 1,2-bis(9-bora-1,2,3,4,5,6,7,8-octafluorofluorenyl)-3,4,5,6-tetrafluorobenzene is provided. Methods for making analogs of the compound are also provided.

In a further aspect, the present invention provides a method for making 1,2-bis[di(perfluorophenyl)boryl]-3,4,5,6-tetrafluorobenzene($1,2-[B(C_6F_5)_2]_2C_6F_4$).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Perfluoroaryl boranes of general formula B(ArF)$_3$ (where ArF is a completely fluorinated aromatic group, for example, pentafluorophenyl (C$_6$F$_5$)) are technologically important co-catalysts in olefin polymerization catalyst systems (see, for example, Marks and Chen, *Chem. Rev.* 2000, 100, 1391). Some years ago, 1,2-bis[di(perfluorophenyl)boryl]-3,4,5,6-tetrafluorobenzene (or 1,2-[B(C$_6$F$_5$)$_2$]$_2$C$_6$F$_4$), a derivative of this class of boranes that contains two perfluoroaryl borane centers arrayed next to each other on an aromatic backbone, was prepared. The preparation and some applications of this compound has been described. See, for example, Williams, V. C.; Piers, W. E.; Clegg, W.; Collins, S.; Marder, T. B. "New Bifunctional Perfluoroaryl Boranes. Synthesis and Reactivity of the ortho-Phenylene Bridged Diboranes 1,2-[B(C$_6$F$_5$)$_2$]$_2$C$_6$X$_4$ (X=H, F)." *J. Am. Chem. Soc.* 1999, 121, 3244; Williams, V. C.; Dai, C.; Li, Z.; Collins, S.; Piers, W. E.; Clegg, W. C.; Elsegood, M. R. J.; Marder, T. B. "Activation of Cp$_2$ZrMe$_2$ with New Perfluoroaryl Diboranes: Solution Chemistry and Ethylene Polymerization Behavior in the Presence of MeAl(BHT)$_2$." *Angew. Chem. Int. Ed.* 1999, 38, 3695; Williams, V. C.; Irvine, G. J.; Piers, W. E.; Li, Z.; Collins, S.; Clegg, W.; Elsegood, M. R. J.; Marder, T. B. "Novel Trityl Activators with New Weakly Coordinating Anions Derived From 1,2-[B(C$_6$F$_5$)$_2$]$_2$C$_6$F$_4$: Synthesis, Structures and Olefin Polymerization Behavior" *Organometallics* 2000, 19, 1619; and Henderson, L. H.; Piers, W. E.; McDonald, R. "Anion Stability in Stannylium, Oxonium and Silylium Salts of the Weakly Coordinating Anion [C$_6$F$_4$-1,2-{B(C$_6$F$_5$)$_2$}$_2$(µ-OCH$_3$)]$^-$" *Organometallics* 2002, 21, 340.

The utility of this compound as an initiator in the polymerization of isobutylene, the product of which is butyl rubber, the main component of tire rubber, has been described. The unique properties of this catalyst have led to some potentially revolutionary discoveries for this industrially important process. The efficacy of 1,2-[B(C$_6$F$_5$)$_2$]$_2$C$_6$F$_4$ under both traditional conditions and aqueous emulsion conditions has been described. The use of 1,2-[B(C$_6$F$_5$)$_2$]$_2$C$_6$F$_4$ under traditional conditions is described in Lewis, S. P.; Taylor, N. J.; Piers, W. E.; Collins, S. "Isobutene Polymerization Using a Chelating Diborane Initiator." *J. Am. Chem. Soc.* 2003, 125, 14686.

Figure 1:
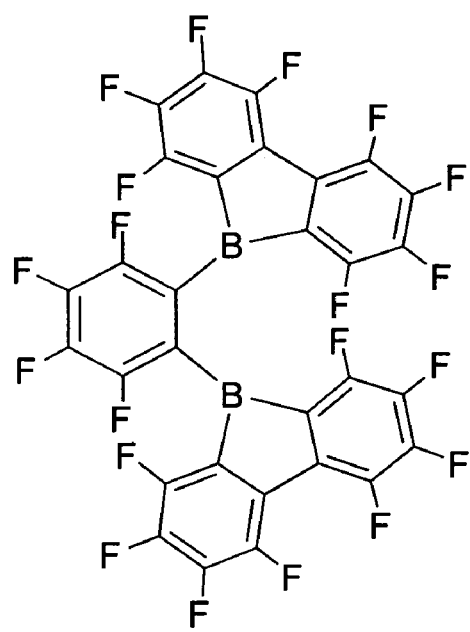
FIG. 1 is the chemical structure of 1,2-bis(9-bora-1,2,3,4,5,6,7,8-octafluorofluorenyl)-3,4,5,6-tetrafluorobenzene.

In one aspect, the present invention provides 1,2-bis(9-bora-1,2,3,4,5,6,7,8-octafluorofluorenyl)-3,4,5,6-tetrafluorobenzene (also referred to herein as 1,2-[B(C$_{12}$F$_8$)]$_2$C$_6$F$_4$ and Compound I). The chemical structure of 1,2-[B(C$_{12}$F$_8$)]$_2$ C$_6$F$_4$) is shown in FIG. 1. Compound I differs from 1,2-bis[di(perfluorophenyl)boryl]-3,4,5,6-tetrafluorobenzene (also referred to herein as 1,2-[B(C$_6$F$_5$)$_2$]$_2$C$_6$F$_4$ and Compound II) in that Compound II has two monovalent perfluorophenyl (i.e., C$_6$F$_5$) substituents on each of the boron centers, whereas Compound I has a single divalent perfluorofluorenyl (i.e., C$_{12}$F$_8$) substituent that constrains each boron center into a borole ring framework. Thus, while Compound II is a diborane having boron substituents that are monovalent (i.e., C$_6$F$_5$), Compound I is a diborole having boron substituents that are divalent (i.e., C$_{12}$F$_8$).

The present invention provides diborane and diborole compounds that as useful as initiators in olefin polymerization. A description of the use of Compound I as an initiator in ethylene polymerization is described in Example 3.

The compounds of the invention can also be used as catalysts in the dehydrogenerative silation of alcohols. A representative method for silation of alcohols using B(C$_6$F$_5$)$_3$ as a catalyst is described by Piers et al. in *J. Org. Chem.* 1999, 64, 4887–4892, incorporated herein by reference in its entirety. The compounds of the invention can also be used as catalysts in the hydrosilation of compounds including carbonyl groups. A representative method for hydrosilation of carbonyl groups using B(C$_6$F$_5$)$_3$ as a catalyst is described by Piers et al. in *J. Org. Chem.* 2000, 64, 4887–4892, incorporated herein by reference in its entirety.

A major drawback for the use of Compounds I and II as initiators in olefin polymerization processes lies in the synthetic procedures required to produce Compounds I and II, which up to now have involved the use of a highly toxic and undesirable organomercury reagent. The present invention provides an environmentally friendly and economical synthesis of each of the two compounds. A schematic illustration of the syntheses of Compounds I and II is shown in FIG. 2.

Figure 2:
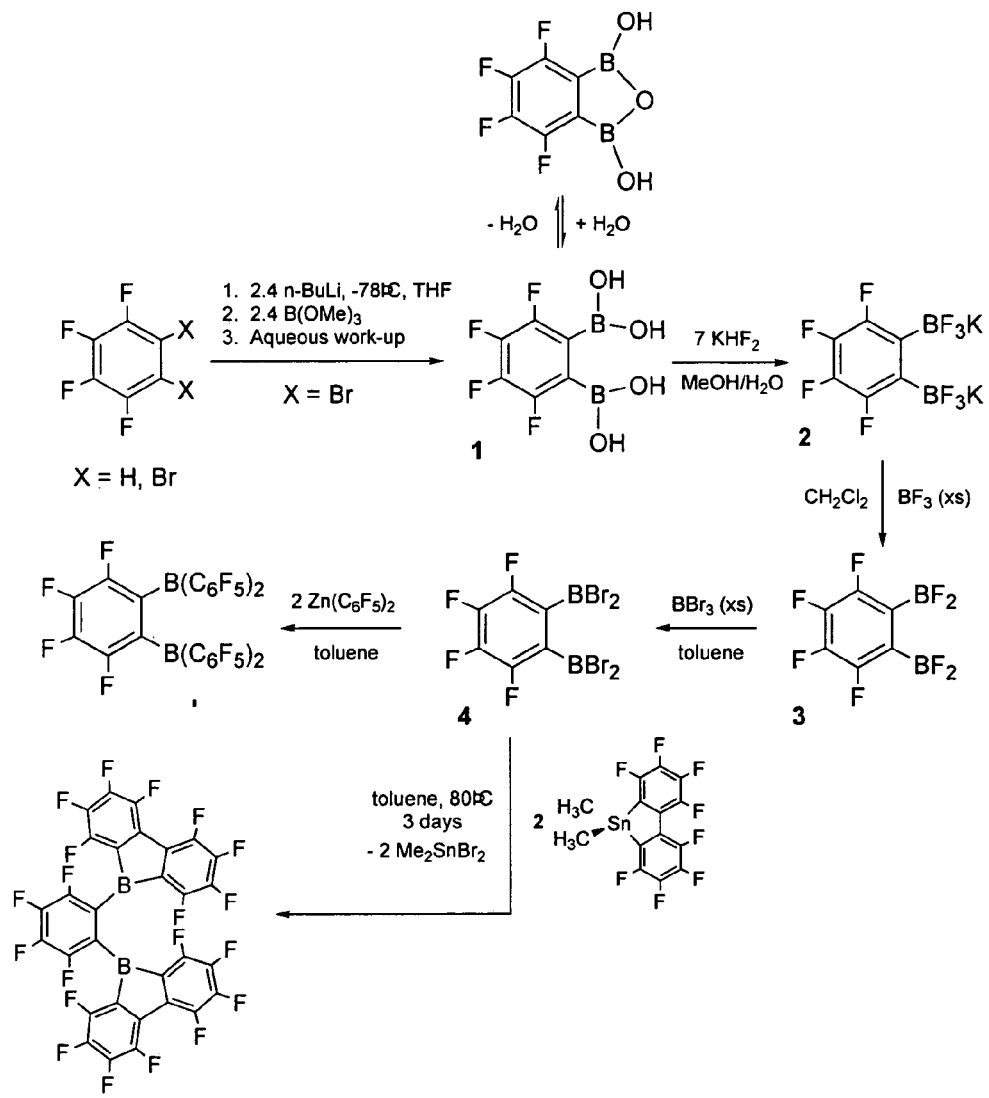
FIG. 2 is a schematic illustration of a representative method of the invention for synthesizing 1,2-bis(9-bora-1,2,3,4,5,6,7,8-octafluorofluorenyl)-3,4,5,6-tetrafluorobenzene.

Referring to FIG. 2, the synthetic route starts with tetrafluorodibromobenzene, which was converted to bis-boronic acid 1. The bis-boronic acid 1 was formed in good yield (75%) and then converted to the dipotassium salt of bis-trifluoroborate 2. Sequential treatment with boron trifluoride (BF$_3$) and then boron tribromide (BBr$_3$) converted bis-trifluoroborate 2 into bis-dibromoboryl compound 4, from which both Compounds I and II were prepared. Thus, the preparation of bis-dibromoboryl compound 4 constitutes a formal synthesis of Compounds I and II. The synthesis of Compound I is described in Example 1. The synthesis of Compound II is described in Example 2.

Thus, in another aspect of the present invention, a method for making 1,2-bis(9-bora-1,2,3,4,5,6,7,8-octafluorofluorenyl)-3,4,5,6-tetrafluorobenzene (Compound I) is provided. In one embodiment, the method includes the following steps:

(a) reacting a 1,2-salt of 3,4,5,6-tetrafluorobenzene with a trialkylborate to provide a bis-boronic acid ester and hydrolyzing the bis-boronic acid ester to provide 1,2-bis[(dihydroxy)boryl]tetrafluorobenzene;

(b) reacting 1,2-bis[(dihydroxy)boryl]tetrafluorobenzene with a hydrogen difluoride salt to provide a tetrafluorophenyl-bis-1,2-trifluoroborate salt;

(c) reacting a tetrafluorophenyl-bis-1,2-trifluoroborate salt with boron trifluoride to provide 1,2-bis(difluoroboryl) tetrafluorobenzene;

(d) reacting 1,2-bis(difluoroboryl)tetrafluorobenzene with boron tribromide to provide 1,2-bis(dibromoboryl)tetrafluorobenzene; and (e) reacting 1,2-bis(dibromoboryl)tetrafluorobenzene with a 9-(dialkyltin) perfluorofluorene to provide 1,2-bis(9-bora-1,2,3,4,5,6,7,8-octafluorofluorenyl)-3,4,5,6-tetrafluorobenzene.

In another aspect of the present invention, a method for making 1,2-bis[di(perfluorophenyl)boryl]-3,4,5,6-tetrafluorobenzene (Compound II) is provided. In one embodiment, the method includes steps (a) through (d) above followed by reacting 1,2-bis(dibromoboryl)tetrafluorobenzene with di(perfluorophenyl)zinc, $Zn(C_6F_5)_2$, to provide 1,2-bis[di (perfluorophenyl)boryl]-3,4,5,6-tetrafluorobenzene.

In one embodiment of the above methods, the 1,2 salt of 3,4,5,6-tetrafluorobenzene is a 1,2-dilithium salt. In one embodiment, the 1,2-dilithium salt is made by reacting 1,2-dibromo-3,4,5,6-tetrafluorobenzene with n-butyl lithium.

In one embodiment of the above methods, the trialkylborate is trimethylborate. Suitable alkyl groups include any alkyl group that permits the reaction to proceed efficiently under convenient reaction conditions. Examples of suitable alkyl groups include C1–C12 alkyl groups.

In one embodiment of the above methods, the hydrogen difluoride salt is potassium hydrogen difluoride.

In one embodiment of the above methods, the tetrafluorophenyl-bis-1,2-trifluoroborate salt is potassium tetrafluorophenyl-bis-1,2-trifluoroborate.

In one embodiment of the method for making 1,2-[B $(C_{12}F_8)]_2C_6F_4$, the 9-(dialkyltin) perfluorofluorene is 9-(dimethyltin) perfluorofluorene. In another embodiment, the 9-(dialkyltin) perfluorofluorene is 9-(dibutyltin) perfluorofluorene.

In another aspect of the invention, analogs of Compound I and Compound II, and methods for making the analogs are provided. Compounds I and II are 1,2-phenyl substituted compounds. Compound I includes a 1,2-perfluorophenyl "backbone" structure to which are covalently coupled two 9-bora-perfluorofluorenyl (i.e., $-B(C_{12}F_8)$) substituents. Similarly, Compound II includes a 1,2-perfluorophenyl "backbone" structure to which are covalently coupled two boryl di(perfluorophenyl) (i.e., $-B(C_6F_5)_2$) substituents. In addition to compounds having 1,2-phenyl backbone structures, the present invention provides compounds having other backbone structures. Representative backbone structures other than 1,2-phenyl backbone structures are illustrated in FIGS. 3–15. In FIGS. 3–15, $Ar^F$ represents a perfluoroaryl group. In these figures, the perfluoroaryl groups are represented as either $Ar^F$ (e.g., $C_6F_5$, monovalent perfluorophenyl) or $Ar^F_2$ (e.g., $C_{12}F_8$, divalent perfluorofluorene). It will be appreciated that other perfluoroaryl groups are within the scope of the invention.

Figure 3:
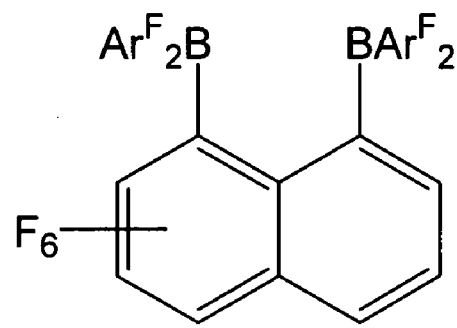
FIG. 3 is a schematic illustration of the chemical structure of a representative compound of the invention, a 1,8-bis($BAr^F_2$)hexafluoronaphthalene compound.

FIG. 3 is a schematic illustration of the chemical structure of a representative compound of the invention, a 1,8-bis $(BAr^F_2)$hexafluoronaphthalene compound.

Figure 4:
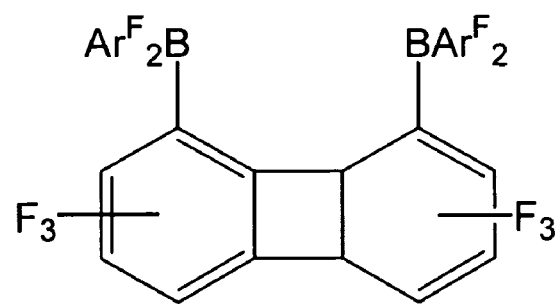
FIG. 4 is a schematic illustration of the chemical structure of a representative compound of the invention, a 1,8-bis($BAr^F_2$)hexafluorobiphenylene compound.
Figure 4:

FIG. 4 is a schematic illustration of the chemical structure of a representative compound of the invention, a 1,8-bis $(BAr^F_2)$hexafluorobiphenylene compound.

Figure 5:
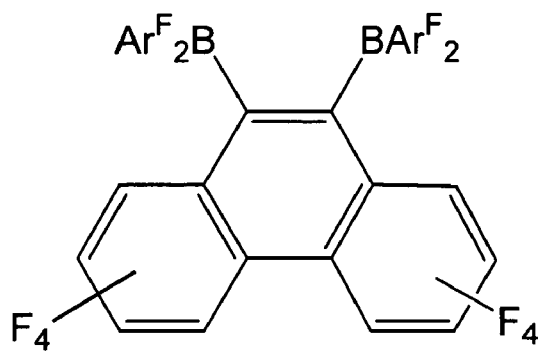
FIG. 5 is a schematic illustration of the chemical structure of a representative compound of the invention, a 9,10-bis($BAr^F_2$)octafluorophenanthrene compound.
Figure 5:

FIG. 5 is a schematic illustration of the chemical structure of a representative compound of the invention, a 9,10-bis $(BAr^F_2)$octafluorophenanthrene compound.

Figure 6:
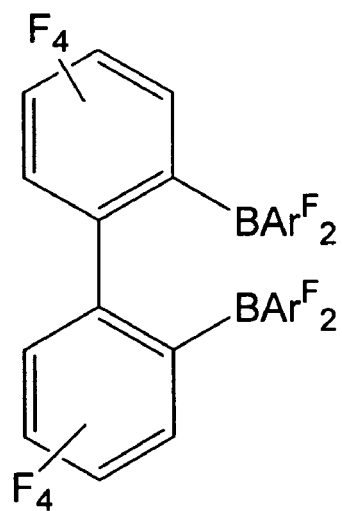
FIG. 6 is a schematic illustration of the chemical structure of a representative compound of the invention, a 2,2'-bis($BAr^F_2$)octafluorobiphenyl compound.

FIG. 6 is a schematic illustration of the chemical structure of a representative compound of the invention, a 2,2'-bis $(BAr^F_2)$octafluorobiphenyl compound.

Figure 7:
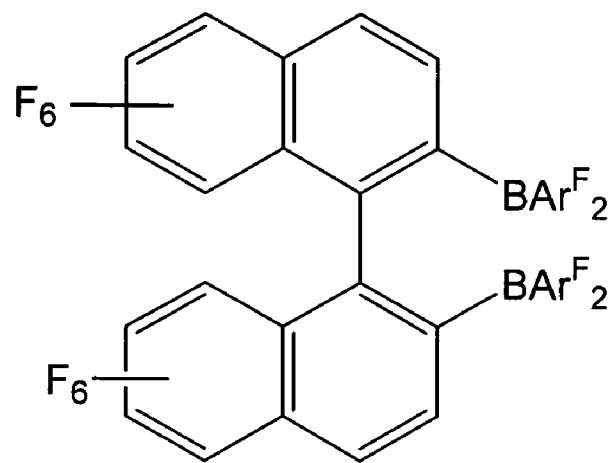
FIG. 7 is a schematic illustration of the chemical structure of a representative compound of the invention, a 2,2'-bis($BAr^F_2$)dodecafluoro-1,1'-binaphthalene compound.

FIG. 7 is a schematic illustration of the chemical structure of a representative compound of the invention, a 2,2'-bis $(BAr^F_2)$dodecafluoro-1,1'-binaphthalene compound.

Figure 8:
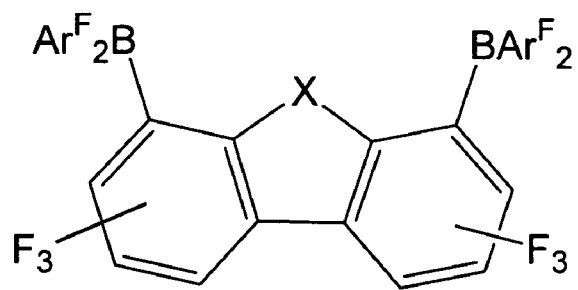
FIG. 8 is a schematic illustration of the chemical structure of representative compounds of the invention; a 1,8-bis($BAr^F_2$)hexafluorofluorene compound when X=$CH_2$; a 1,8-bis($BAr^F_2$)hexafluorocarbazole compound when X=NR; and a 1,8-bis($BAr^F_2$)hexafluorodibenzofuran compound when X=O.

FIG. 8 is a schematic illustration of the chemical structure of representative compounds of the invention; a 1,8-bis $(BAr^F_2)$hexafluorofluorene compound when X=$CH_2$; a 1,8-bis$(BAr^F_2)$hexafluorocarbazole compound when X=NR; and a 1,8-bis$(BAr^F_2)$hexafluorodibenzofuran compound when X=O.

Figure 9:
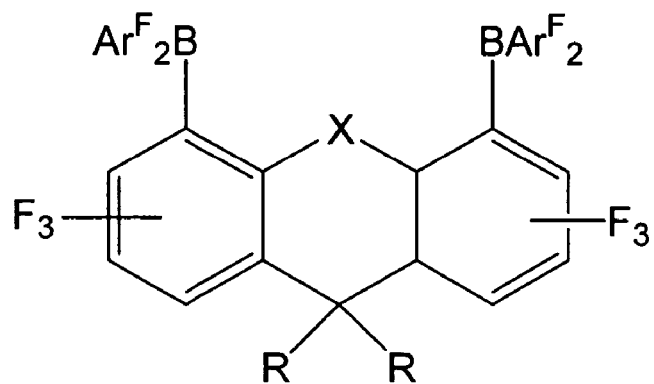
FIG. 9 is a schematic illustration of the chemical structure of representative dihydroanthracene compounds of the invention; a 1,8-bis($BAr^F_2$)-10,10-disubstituted-hexafluorodihydroanthracene compound when X=$CH_2$; a 1,8-bis($BAr^F_2$)-10,10-disubstituted-9-aza-hexafluorodihydroanthracene compound when X=NR; and a 1,8-bis($BAr^F_2$)-10,10-disubstituted-9-oxo-hexafluorodihydroanthracene compound when X=O.

FIG. 9 is a schematic illustration of the chemical structure of representative dihydroanthracene compounds of the invention; a 1,8-bis$(BAr^F_2)$-10,10-disubstituted-hexafluorodihydroanthracene compound when X=$CH_2$; a 1,8-bis $(BAr^F_2)$-10,10-disubstituted-9-aza-hexafluorodihydroanthracene compound when X=NR; and a 1,8-bis$(BAr^F_2)$-10,10-disubstituted-9-oxo-hexafluorodihydroanthracene compound when X=O.

Figure 10:
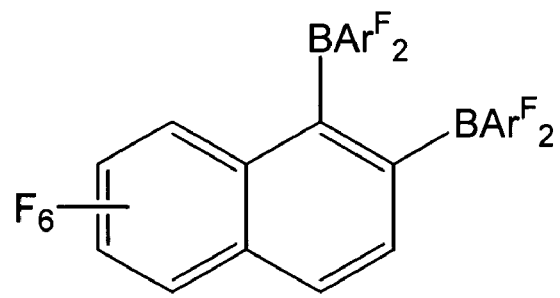
FIG. 10 is a schematic illustration of the chemical structure of a representative compound of the invention, a 1,2-bis($BAr^F_2$)hexafluoronaphthalene compound.
Figure 10:

FIG. 10 is a schematic illustration of the chemical structure of a representative compound of the invention, a 1,2-bis$(BAr^F_2)$hexafluoronaphthalene compound.

Figure 11:
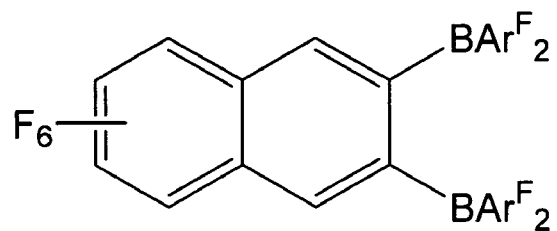
FIG. 11 is a schematic illustration of the chemical structure of a representative compound of the invention, a 2,3-bis($BAr^F_2$)hexafluoronaphthalene compound.
Figure 11:

FIG. 11 is a schematic illustration of the chemical structure of a representative compound of the invention, a 2,3-bis$(BAr^F_2)$hexafluoronaphthalene compound.

Figure 12:
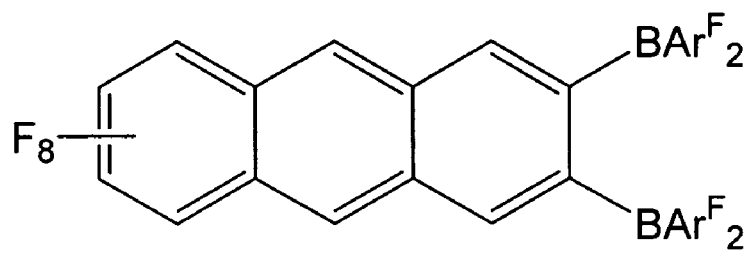
FIG. 12 is a schematic illustration of the chemical structure of a representative compound of the invention, a 2,3-bis($BAr^F_2$)octafluoroanthracene compound.

FIG. 12 is a schematic illustration of the chemical structure of a representative compound of the invention, a 2,3-bis$(BAr^F_2)$octafluoroanthracene compound.

Figure 13:
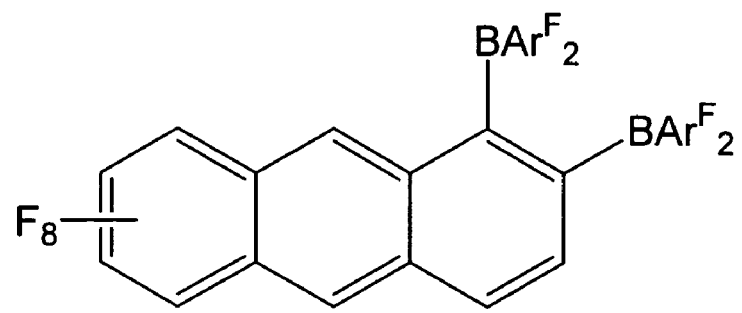
FIG. 13 is a schematic illustration of the chemical structure of a representative compound of the invention, a 1,2-bis(BAr$^F{}_2$)octafluoroanthracene compound.
Figure 13:

FIG. 13 is a schematic illustration of the chemical structure of a representative compound of the invention, a 1,2-bis$(BAr^F_2)$octafluoroanthracene compound.

Figure 14:
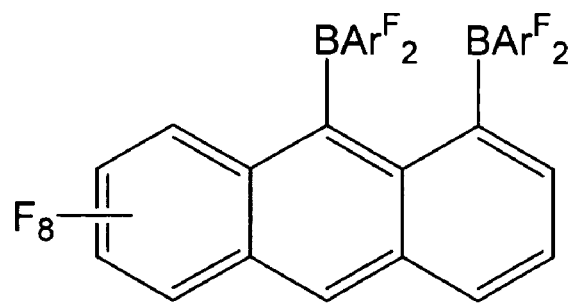
FIG. 14 is a schematic illustration of the chemical structure of a representative compound of the invention, a 1,9-bis(BAr$^F{}_2$)octafluoroanthracene compound.

FIG. 14 is a schematic illustration of the chemical structure of a representative compound of the invention, a 1,9-bis$(BAr^F_2)$octafluoroanthracene compound.

Figure 15:
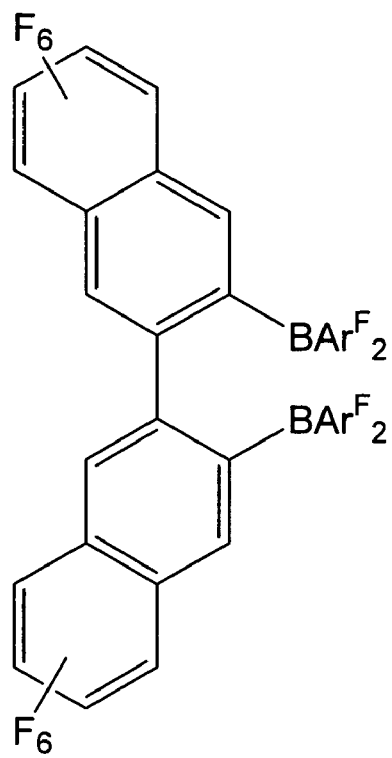
FIG. 15 is a schematic illustration of the chemical structure of a representative compound of the invention, a 3,3'-bis(BAr$^F{}_2$)dodecafluoro-2,2'-binaphthalene compound.

FIG. 15 is a schematic illustration of the chemical structure of a representative compound of the invention, a 3,3'-bis$(BAr^F_2)$dodecafluoro-2,2'-binaphthalene compound.

The compounds of the invention are aryl compounds that bear two boron centers directly bonded to a carbon atom of an aromatic ring of the aryl compound. As illustrated in FIGS. 1 and 3–15, the boron centers can be bonded to a monocyclic aromatic (see, for example, FIG. 1) or polycyclic aromatic (see, for example, FIGS. 3, 5, and 10–14). The boron centers can be bonded to the same ring of a polycyclic aromatic (see, for example, FIGS. 5 and 10–13). Alternatively, the boron centers can be bonded to different rings of a polycyclic aromatic (see, for example, FIGS. 3 and 14). In addition to monocyclic and polycyclic aromatic compounds, suitable backbone structures also include compounds having two aromatic rings (see, for example, FIGS. 4, 6–9, and 15). For these compounds, one boron center is bonded to a carbon atom of one aromatic ring and the second boron center is bonded to a carbon atom of a second aromatic ring.

The syntheses of Compounds I and II are illustrated in FIG. 2. By appropriate selection of the starting material (e.g., $C_6F_4X_2$ in FIG. 2), a variety of diborane and diborole compounds (e.g., the compounds illustrated in FIGS. 3–15) can be similarly prepared. In the method, an appropriate starting material (e.g., dihalo, hydrogen, or other suitably substituted aryl compound) is converted to a bis-boronic acid. The bis-boronic acid is then converted to the dipotassium salt of the bis-trifluoroborate. Sequential treatment with boron trifluoride ($BF_3$) and then boron tribromide ($BBr_3$) converts the bis-trifluoroborate into a bis-dibromoboryl compound, from which the final compounds can be prepared. The bis-dibromoboryl compound can be treated with the 9-(dimethyltin)perfluorofluorene to provide the corresponding 9-borafluorenyl compounds (i.e., diborole compounds). Alternatively, the bis-dibromoboryl compound can be treated with an appropriate organometallic reagent (e.g., di(perfluorophenyl) zinc) to provide the corresponding diboranes. Thus, the present invention provides a general synthetic methodology for aryl compounds substituted with either two borole centers (i.e., aryl diborole) or two borane centers (i.e., aryl diborane).

The following examples are provided for the purpose of illustrating, not limiting, the invention.

EXAMPLES

Example 1

Synthesis of 1,2-bis(9-Bora-1,2,3,4,5,6,7,8-octafluorofluorenyl)-3,4,5,6-tetrafluorobenzene: 1,2-[B($C_{12}F_8$)]$_2C_6F_4$ General Considerations. NMR spectra were measured on a Bruker Avance DRX-400 ($^{11}$B at 128.41 MHz) and a Bruker AMX2-300 ($^{19}$F at 282.41 MHz). $^{11}$B NMR spectra were referenced relative to $BF_3 \cdot Et_2O$ at 0 ppm. $^{19}$F NMR spectra were referenced externally to $C_6F_6$ at −163 ppm relative to $CFCl_3$ at 0 ppm. 1,2-Dibromotetrafluorobenzene (Aldrich), 1.6 M BuLi (Aldrich), $KHF_2$ (Aldrich), and $BF_3$ (Aldrich) were used as supplied. $B(OCH_3)_3$ (Aldrich) was distilled over Na prior to use and $BBr_3$ (Aldrich) was distilled from Cu wire prior to use.

All manipulations with aryldihalogenboranes were performed using standard vacuum and Schlenk techniques or in a glovebox under an atmosphere of argon. $CH_2Cl2$ was distilled from $CaH_2$ prior to use. $CD_2Cl_2$ and $C_6D_6$ were purchased from Cambridge Isotopes and rigorously dried then distilled from $CaH_2$ and Na/benzophenone respectively. $CD_3CN$ and $D_2O$ were purchased from Cambridge Isotopes and Aldrich, respectively, and used as is.

The synthesis of 1,2-bis(9-bora-1,2,3,4,5,6,7,8-octafluorofluorenyl)-3,4,5,6-tetrafluorobenzene described below is schematically illustrated in FIG. 2.

Synthesis of 1,2-bis[(Dihydroxy)boryl]tetrafluorobenzene (1). Butyllithium (1.6 M in hexanes, 12.6 mL, 20.16 mmol) was added dropwise to a stirred solution of 1,2-dibromotetrafluorobenzene (2.6 g, 8.44 mmol) in ether (50 mL) at −78° C. After 2 hours this solution was slowly added to a pre-cooled solution (−78° C.) of trimethylborate (2.3 mL, 20.52 mmol) in ether (25 mL). The resulting suspension was stirred at −78° C. for two hours then gradually warmed to room temperature and hydrolyzed with 20 mL of 10% HCl. The yellow organic phase was separated and the aqueous phase was extracted with dichloromethane (3×15 mL). The combined organic phases were washed with water (3×10 mL) and dried over magnesium sulfate. Removal of solvent under reduced pressure gave a yellow oil that was recrystallized from water at a pH of 4 to afford a crystalline solid. (1.5 g, 75%) $^{19}$F NMR ($D_2O$/HCl) δ: −136.6 (d, $J_{F\text{-}F}$=28.3 Hz, 2F, $C_6F_4$), −156.5 (d, $J_{F\text{-}F}$=28.3 Hz, 2F, $C_6F_4$). $^{11}$B NMR ($D_2O$/HCl) δ: 16.

Synthesis of Potassium Tetrafluorophenyl-bis-1,2-trifluoroborate (2). A solution of the bis-boronic acid 1 (2.4 g, 10.11 mmol) in methanol (20 mL) was added to a stirred solution of potassium hydrogenfluoride (5.5 g, 70.41 mmol) in water (40 mL) and stirred for 1 hour. The solution was filtered and the solid was washed with water (3×10 mL) then ether (3×10 mL) and dried under reduced pressure. The product was recrystallized from hot acetonitrile affording an off-white solid (1.04 g, 28%). $^{19}$F NMR ($CD_3CN$/$D_2O$) δ: −139.0 (d, $J_{F\text{-}F}$=28.2 Hz, 2F, $C_6F_4$), −144.1 (m, 6F, —$BF_3$), −160.1 (d, $J_{F\text{-}F}$=28.2 Hz, 2F, $C_6F_4$). $^{11}$B NMR ($CD_3CN$/$D_2O$) δ: 3.9 (multiplet).

Synthesis of 1,2-bis(Difluoroboryl)tetrafluorobenzene (3). An excess of boron trifluoride gas was introduced to a stirred suspension of the potassium aryltrifluoroborate salt 2 (1.0 g, 27.32 mmol) in dichloromethane in a thick walled bomb at −40° C. After 30 minutes the solution was degassed under vacuum at −78° C. The resultant red colored solution was filtered and the remaining solid was washed with dichloromethane (2×5 mL). A deep red liquid was obtained after the solvent was distilled from product under reduced pressure. (0.4 g, 60%). $^{19}$F NMR ($CD_2Cl_2$) δ: −72.4 (br. s, 4F, —$BF_2$), −126.9 (m, 2F, $C_6F_4$), −146.5 (m, 2F, $C_6F_4$). $^{11}$B NMR ($CD_2Cl_2$) δ: 22.6 (br m).

Synthesis of 1,2-bis(Dibromoboryl)tetrafluorobenzene (4). Boron tribromide (0.76 g, 3.05 mmol) was introduced to a solution of 3 (0.15 g, 0.61 mmol) in toluene (5 mL) in a thick walled bomb at −78° C. The bomb was sealed and heated at 60° C. for 30 minutes. Volatiles were removed under reduced pressure to afford the desired product. (0.25 g, 85%). $^{19}$F NMR ($C_6D_6$) δ: −125.7 (m, 2F, $C_6F_4$), −147.3 (m, 2F, $C_6F_4$). $^{11}$B NMR ($C_6D_6$) δ: 54 (br).

Synthesis of 1,2-bis[9-Bora-1,2,3,4,5,6,7,8-octafluorofluorenyl)tetrafluorobenzene (Compound I). $C_{12}F_8SnMe_2$ (0.786 g, 1.77 mmol) and $C_6F_4(BBr_2)_2$ (0.435 g, 0.84 mmol) were dissolved in toluene (20 ml), sealed in glass bomb equipped with a Kontes valve and heated to 85° C. for 36 hours. The solvent was removed in vacuo and the $Me_2SnBr_2$ by-product was removed via sublimation (30° C., 0.01 mm Hg). The sublimation residues were placed in a frit assembly and hexanes (30 ml) was condensed into the flask. The solution was cooled to −78° C. and stirred for 1 hour. The solution was cold filtered and a light yellow solid was obtained and dried in vacuo. Yield: 0.520 g, 81.2%. $^{19}$F NMR ($C_6D_6$): δ−121.1 (br, 4F), −123.6 (aa'bb' pattern, 2F), −128.9 (br, 4F), −138.6 (br, 4F), −148.6 (aa'bb' pattern, 2F), −151.9 (br, 4F). $\lambda_{max}$ (hexanes) 425 nm ε=5.9×10$^2$ L mol$^{-1}$ cm$^{-1}$. Anal. Calcd. for $C_{30}F_{20}B_2$: C 47.29. Found: C 47.78.

Example 2

Synthesis of 1,2-bis[Di(perfluorophenyl)borvl]-3,4,5,6-tetrafluorobenzene: 1,2-[B($C_6F_5$)$_2$]$_2C_6F_4$ The synthesis of 1,2-bis[di(perfluorophenyl)boryl]-3,4,5,6-tetrafluorobenzene (1,2-[B($C_6F_5$)$_2$]$_2C_6F_4$) (Compound II) described below is schematically illustrated in FIG. 2.

Compound II was prepared from 1,2-bis(dibromoboryl) tetrafluorobenzene (4), prepared as described above in Example 1.

Toluene (25 ml) was condensed into an evacuated bomb containing $Zn(C_6F_5)_2$ (1.40 g, 3.50 mmol) at −78° C. To this colorless solution was added boran 1,2-bis-(dibromoboryl) tetrafluorobenzene (0.84 g, 1.73 mmol) as a neat liquid. The mixture was heated at 80° C. for 12 hours, after which the toluene was removed under reduced pressure. The white residue was extracted using toluene (40 ml), filtered and concentrated. The product was isolated after crystallization from hot toluene and washing with cold hexanes (0.8 g, 0.95 mmol, 55%). $^{19}$F NMR ($C_6D_6$) δ−127.6 (m, 2F, $C_6F_4$); −128.5 (d, 8F, o-$C_6F_5$); −141.6 (m, 2F, $C_6F_4$); −148.9 (m, 4F, p-$C_6F_5$); −161.5 (m, 8F, m-$C_6F_5$). Anal. Calcd. for $C_{30}B_2F_{24}$: C, 42.9. Found: C, 42.5.

Example 3

Polymerization of Ethylene with Zirconocene/9-Borafluorene Catalyst Systems

This example describes the use of 9-borafluorene Lewis acids as co-catalysts in the realm of metallocene catalyzed olefin polymerization. The bifunctional 9-borafluorene was found to react with only one equivalent of zirconocene methyl but the additional Lewis acidic group may be involved in lowering the barrier to exchange via a boron/methyl interaction in the exchange transition state. The chelated ring structure of the 9-borafluorene Lewis acids has been exploited in the stabilization of the produced ion pairs by preventing fluoroaryl ring transfer as a catalyst deactivation mechanism. The complex produced with the methyl substituted 9-borafluorene 5 undergoes methane elimination at elevated temperatures to produce a μ-methylene bridged zirconium species, $Cp_2Zr(Me)$—$CH_2$—$B(Me)(C_{12}F_8)$. The 9-borafluorenes were evaluated as co-catalysts for ethylene polymerization and found to be comparable to analogous fluoroaryl boranes. The thermal stability of the methyl substituted ion pair catalyst was also evaluated by an incubation ethylene polymerization experiment.

Ethylene Polymerization. The polymerization of ethylene was performed at 25° C. and 1 atm. pressure in dilute, ethylene saturated solutions of toluene using modified, Schleck-type glassware and gas tight syringes equipped with Teflon stopcocks. The prototype pre-catalyst, dimethyl zirconocene, has been used as a standard for many other fluoroaryl borane systems.

The polymerization activities of the 9-borafluorene Lewis acids have been collected along with data for related fluoroaryl borane co-catalysts (see Table 1). All reported values are the average of at least 2 separate runs. In line with the determined Lewis acidity each of the Lewis acids and the nature of the active catalyst, the polymerization activity of the catalyst/co-catalyst system increases with increasing Lewis acidity of the boron-based Lewis acidic co-catalyst. This is best illustrated in the comparison of methyl-9-boraperfluorofluorene compound (Compound III) and perfluorophenyl-9-bora-perfluorofluorene compound (Compound IV) where the activity of the weaker Lewis acid, Compound III, is about one order of magnitude less than that of Compound IV. Also, Lewis acids of comparable Lewis acidity, $MeB(C_6F_5)_2$ and Compound III, for instance, have approximately equivalent activities. As shown in the solution and solid state based studied of the bifinctional 9-borafluorene (Compound I), the ion pair/active catalyst formed is very similar to that formed with Compound IV. In accord with this observation, the polymerization activity of the catalyst formed with Compound I is close to that of Compound IV. The activities observed for both Compound IV and Compound I are high enough to be industrially important

TABLE 1

Activity values for ethylene polymerization.

| Co-catalyst | Co-catalyst Amount (mg) | Catalyst Amount (mg) | Polymer (g) | Time (sec) | Activity |
|---|---|---|---|---|---|
| IV | 14 | 7 | 0.427 | 120 | $4.58 \times 10^5$ |
| $B(C_6F_5)_3$ | 20 | 10 | 0.495 | 164 | $2.73 \times 10^5$ |
| III | 9 | 7 | 0.130 | 724 | $2.34 \times 10^4$ |
| $MeB(C_6F_5)_2$ | 15 | 10.5 | 0.161 | 725 | $1.91 \times 10^4$ |
| I | 31 | 10 | 0.302 | 122 | $2.24 \times 10^5$ |

Activities are reported in units of $g\ mol(Zr)^{-1}\ atm^{-1}\ h^{-1}$.

General procedure for ethylene polymerization experiments. Ethylene polymerizations were carried out in 100 ml Schlenk type flasks, which have been modified to allow a rubber septa to be placed over the side arm, and were equipped with large, oval shaped stirbars. The catalyst, $Cp_2ZrMe_2$ (7–11 mg), was dissolved in toluene (45 ml), the solution was degassed three times via the freeze-pump-thaw method, saturated with ethylene (1 atm) for at least 5 minutes and placed in a 25° C. constant temperature water bath. Co-catalyst (1.1 equivalents) was dissolved in toluene (5.0 ml) and injected into the catalyst/ethylene solution via a gas tight syringe through the Schlenk side arm. Polymerizations were quenched with 1:3 HCl/MeOH (5.0 ml) and MeOH (75 ml) was added to precipitate the polymer, which was suction filtered, washed with MeOH (3×30 ml) and dried under high vacuum overnight.

While the preferred embodiment of the invention has been illustrated and described, it will be appreciated that various changes can be made therein without departing from the spirit and scope of the invention.

What is claimed is:

1. A method for making 1,2-bis(9-bora-1,2,3,4,5,6,7,8-octafluorofluorenyl)-3,4,5,6-tetrafluorobenzene having the structure

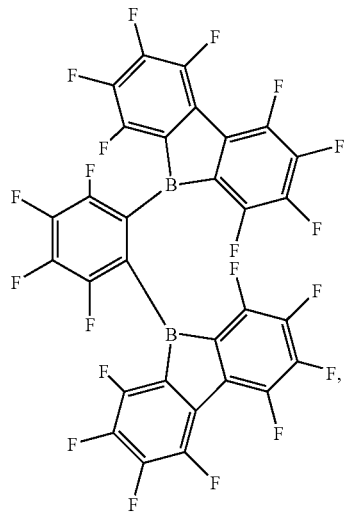

comprising:
(a) reacting a 1,2-salt of 3,4,5,6-tetrafluorobenzene with a trialkylborate to provide a bis-boronic acid ester and hydrolyzing the bis-boronic acid ester to provide bis-1,2-[(dihydroxy)boryl]tetrafluorobenzene;
(b) reacting bis-1,2-[(dihydroxy)boryl]tetrafluorobenzene with a hydrogen difluoride salt to provide a tetrafluorophenyl-bis-1,2-trifluoroborate salt;
(c) reacting a tetrafluorophenyl-bis-1,2-trifluoroborate salt with boron trifluoride to provide 1,2-bis(difluoroboryl)tetrafluorobenzene;
(d) reacting 1,2-bis(difluoroboryl)tetrafluorobenzene with boron tribromide to provide 1,2-bis(dibromoboryl)tetrafluorobenzene; and
(e) reacting 1,2-bis(dibromoboryl)tetrafluorobenzene with a 9-(dialkyltin) perfluorofluorene to provide 1,2-bis(9-bora-1,2,3,4,5,6,7,8-octafluorofluorenyl)-3,4,5,6-tetrafluorobenzene.

2. The method of claim 1, wherein the 1,2 salt of 3,4,5,6-tetrafluorobenzene is a 1,2-dilithium salt.

3. The method of claim 2, wherein the 1,2-dilithium salt is made by reacting 1,2-dibromo-3,4,5,6-tetrafluorobenzene with n-butyl lithium.

4. The method of claim 1, wherein the trialkylborate is trimethylborate.

5. The method of claim 1, wherein the hydrogen difluoride salt is potassium hydrogen difluoride.

6. The method of claim 1, wherein the tetrafluorophenyl-bis-1,2-trifluoroborate salt is potassium tetrafluorophenyl-bis-1,2-trifluoroborate.

7. The method of claim 1, wherein the 9-(dialkyltin) perfluorofluorene is 9-(dimethyltin) perfluorofluorene.

8. A method for making 1,2-bis[di(perfluorophenyl)boryl]-3,4,5,6-tetrafluorobenzene, comprising:
- (a) reacting a 1,2-salt of 3,4,5,6-tetrafluorobenzene with a trialkylborate to provide a bis-boronic acid ester and hydrolyzing the bis-boronic acid ester to provide bis-1,2-[(dihydroxy)boryl]tetrafluorobenzene;
- (b) reacting bis-1,2-[(dihydroxy)boryl]tetrafluorobenzene with a hydrogen difluoride salt to provide a tetrafluorophenyl-bis-1,2-trifluoroborate salt;
- (c) reacting a tetrafluorophenyl-bis-1,2-trifluoroborate salt with boron trifluoride to provide 1,2-bis(difluoroboryl)tetrafluorobenzene;
- (d) reacting 1,2-bis(difluoroboryl)tetrafluorobenzene with boron tribromide to provide 1,2-bis(dibromoboryl)tetrafluorobenzene; and
- (e) reacting 1,2-bis(dibromoboryl)tetrafluorobenzene with di(phenylperfluoro) zinc to provide 1,2-bis[di(perfluorophenyl)boryl]-3,4,5,6-tetrafluorobenzene.

9. The method of claim 8, wherein the 1,2 salt of 3,4,5,6-tetrafluorobenzene is a 1,2-dilithium salt.

10. The method of claim 9, wherein the 1,2-dilithium salt is made by reacting 1,2-dibromo-3,4,5,6-tetrafluorobenzene with n-butyl lithium.

11. The method of claim 8, wherein the trialkylborate is trimethylborate.

12. The method of claim 8, wherein the hydrogen difluoride salt is potassium hydrogen difluoride.

13. The method of claim 8, wherein the tetrafluorophenyl-bis-1,2-trifluoroborate salt is potassium tetrafluorophenyl-bis-1,2-trifluoroborate.

* * * * *

UNITED STATES PATENT AND TRADEMARK OFFICE
CERTIFICATE OF CORRECTION

PATENT NO. : 7,078,546 B2
APPLICATION NO. : 10/817753
DATED : July 18, 2006
INVENTOR(S) : W.E. Piers et al.

It is certified that error appears in the above-identified patent and that said Letters Patent is hereby corrected as shown below:

| COLUMN | LINE | ERROR |
|---|---|---|
| (54) Pg. 1, col. 1 | Title | "TETRAFLUROBENZENE" should read --TETRAFLUOROBENZENE -- |
| 1 | 3 | "TETRAFLUROBENZENE" should read --TETRAFLUOROBENZENE -- |
| (57) Pg. 1, col. 2 | Abstract 1-2 of text | "octafluorof-luorenyl)" should break --octafluoro-fluorenyl)-- |

Signed and Sealed this

Thirty-first Day of October, 2006

JON W. DUDAS
*Director of the United States Patent and Trademark Office*